(12) United States Patent
O'Gara et al.

(10) Patent No.: US 12,280,160 B2
(45) Date of Patent: *Apr. 22, 2025

(54) ANTIMICROBIAL BANDAGE

(71) Applicant: HYDROFERA, LLC, Manchester, CT (US)

(72) Inventors: John E. O'Gara, Ashland, MA (US); Eric Lullove, Coconut Creek, FL (US)

(73) Assignee: HYDROFERA, LLC, Manchester, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/240,488

(22) Filed: Aug. 31, 2023

(65) Prior Publication Data

US 2023/0405178 A1 Dec. 21, 2023

Related U.S. Application Data

(63) Continuation of application No. 16/873,525, filed on Apr. 29, 2020, now Pat. No. 11,779,678.

(60) Provisional application No. 62/920,420, filed on Apr. 30, 2019.

(51) Int. Cl.
| | | |
|---|---|---|
| *A61L 15/44* | (2006.01) |
| *A61F 13/00* | (2006.01) |
| *A61F 13/01* | (2024.01) |
| *A61F 13/06* | (2006.01) |
| *A61L 15/24* | (2006.01) |
| *A61L 15/38* | (2006.01) |
| *A61L 15/42* | (2006.01) |

(52) U.S. Cl.
CPC ........ *A61L 15/44* (2013.01); *A61F 13/00059* (2013.01); *A61F 13/00063* (2013.01); *A61F 13/01017* (2024.01); *A61F 13/06* (2013.01); *A61L 15/24* (2013.01); *A61L 15/38* (2013.01); *A61L 15/42* (2013.01); *A61L 15/425* (2013.01); *A61L 2300/216* (2013.01); *A61L 2300/404* (2013.01); *A61L 2300/442* (2013.01)

(58) Field of Classification Search
CPC .......... A61L 15/44; A61L 15/24; A61L 15/38; A61L 15/42; A61L 15/425; A61L 2300/216; A61L 2300/404; A61L 2300/442; A61L 15/28; A61L 15/58; A61F 13/00059; A61F 13/00063; A61F 13/01017; A61F 13/06; A61F 13/08

See application file for complete search history.

(56) References Cited

U.S. PATENT DOCUMENTS

| | | |
|---|---|---|
| 7,507,870 B2 | 3/2009 | Nielsen et al. |
| 8,779,230 B2 | 7/2014 | Murphy et al. |
| 10,179,186 B2 | 1/2019 | Moreland et al. |
| 2006/0030632 A1 | 2/2006 | Krueger et al. |
| 2008/0228123 A1 | 9/2008 | Moore et al. |
| 2009/0112141 A1 | 4/2009 | Derr |
| 2013/0085435 A1 | 4/2013 | Murphy et al. |
| 2014/0018654 A1 | 1/2014 | Drury |
| 2014/0275864 A1 | 9/2014 | Drury |
| 2018/0338945 A1 | 11/2018 | Sambasivam |
| 2020/0129339 A1 | 4/2020 | Drury et al. |
| 2020/0345888 A1 | 11/2020 | O'Gara et al. |
| 2023/0285197 A1 | 9/2023 | Drury et al. |

FOREIGN PATENT DOCUMENTS

| | | |
|---|---|---|
| WO | 9913921 A2 | 3/1999 |

OTHER PUBLICATIONS

Edwards, Karen. New Twist on an Old Favorite: Gentian Violet and Methylene Blue Antibacterial Foams. Advances in Wound Care. vol. 5, No. 1. Jan. 12, 2016. Abstract.

Extended European Search Report issued Jul. 7, 2023 by the European Patent Office in corresponding European Patent Application No. 20798301.6, 13 pages.

Australian Application No. 2020264897; Examination Report No. 1 dated Nov. 29, 2024; 3 pages.

*Primary Examiner* — Jessica Worsham

(74) *Attorney, Agent, or Firm* — CANTOR COLBURN LLP

(57) ABSTRACT

The present invention relates to a compression bandage for treating wounds comprised of a linear elastic compression wrap and a sterilized polymer foam layer containing a plurality of 5 antimicrobial dyes with at least one dye being gram positive and at least one other dye being gram negative and a biofilm reduction agent and wherein said foam is secured to said linear elastic compression wrap.

13 Claims, 4 Drawing Sheets

ANTIMICROBIAL BANDAGE

RELATED APPLICATIONS

This application is a continuation application of application Ser. No. 16/873,525, filed Apr. 29, 2020, which claims priority and benefits from Provisional application Ser. No. 62/920,420 filed Apr. 30, 2019, the contents of which in their entirety are herein incorporated by reference.

STATEMENT REGARDING FEDERALLY SPONSORED RESEARCH OR DEVELOPMENT

None

REFERENCE TO SEQUENCE LISTING, A TABLE OR A COMPUTER PROGRAM LISTING COMPACT DISC APPENDIX

None.

BACKGROUND OF THE INVENTION

1. Field of Invention

The present dressing relates to a compression wrap having a foamed polymeric layer treated with antimicrobial gram positive and gram negative dyes to form a bandage which applies compression while killing or reducing microorganisms such as bacteria, fungi and virus present in the wound being wrapped.

2. Background of the Invention

The use of a compression wrap containing zinc oxide, noble metals, copper and the like for the elimination of bacteria in wrapped wounds is known in the art. These compression wraps are partially successful in that certain bacteria and other microorganisms are reduced in number. However, there are generally remaining bacterial and viral colonies which survive and biofilm quickly forms on the wound requiring that the wound be treated by abrasion. Microorganisms such as fungi, bacteria and viruses in a wound are reduced and/or killed and wound exudate is adsorbed when the present antimicrobial compression wrap is wrapped around the wound coming in direct contact with the wound.

There are a number of compression devices which are used to supply antimicrobial agents to the wound.

U.S. Pat. No. 10,179,186 issued Jan. 15, 2019 discloses the use of antimicrobial zeolites in wound care fabrics, gloves, sleeves, anklets, socks and the like constructed of a first yarn which is used to produce a layer which can be knitted with a second yarn having an antimicrobial agent to form the article. Both the inner layer yarn and the outer layer yarn may be chemically treated with elemental metals, such as gold, copper, iodine, silver, or zinc.

U.S. Pat. No. 8,779,230 issued Jul. 15, 2014 describes a wound treatment system using a wrap having an inner layer of foam material containing impregnated zinc oxide and an outer layer of stretchable compression bandage. In another embodiment a kit is provided including a foam layer impregnated with a zinc oxide containing composition, an elastic bandage of long or short stretch elastic and an outer stocking or sleeve.

U.S. Pat. No. 7,507,870 issued Mar. 24, 2009 is directed toward a wound dressing including a backing layer, an adhesive layer and an absorbent layer between the backing layer and the adhesive layer. The adhesive layer secures the absorbent layer between the backing layer and the adhesive layer. The adhesive layer is interrupted in at least one zone exposing at least a part of the skin contacting surface to the absorbent layer.

There is a limitation on materials that can be used as different adhesives have their properties changed by sterilization. In the case of wound dressings, medical silicone adhesives and silicon rubbers are excluded from use in gamma terminally sterile products, e.g. as cover dressings, despite their excellent clinical performance. Therefore, a wound dressing using a silicone adhesive to adhere the layers to each other or to the skin when combined with an antimicrobial gram positive and gram negative dyed foam material, an enzyme or agent to control or reduce bio-burden together with an elastic outer fabric layer is not known in the prior art.

Wounds often have multiple barriers to healing. None of the aforementioned references teach the use of antimicrobial gram positive and negative dyes in wound treatment or to lessen or preclude bio-film from forming on the wounds. Wound healing and infection is influenced by the relationship between the ability of bacteria to create a stable, prosperous community. Since bacteria are rapidly able to provide protective microenvironment (bio-film) following their attachment to a surface, the ability of the host to control these organisms is likely to decrease as the bio-film community matures. Within a stable biofilm community, interactions between aerobic and anaerobic bacteria are likely to increase their net pathogenic effect, enhancing their potential to cause infection and delay healing. Over the last few years, some researchers have linked bio-film to chronic wounds. Microscopic evaluation of wounds show well organized bio-film with extracellular polymeric substance adhered around colony bacteria in at least 60% of the wounds studied.

There is a need in the art for compression bandages which are antimicrobial and kill/prevent growth of gram positive bacteria and gram negative bacteria, reduce or prevent biofilm, are comfortable during mobility while providing a tight fit and are able to be used with cylindrical compression socks and sleeves. The layered compression wraps allow direct contact of the antimicrobial dyes with the skin and wound of the wearer without abrading or sticking to the wound.

None of the aforementioned prior art references attempt to increase the effect of antimicrobial gram positive and gram negative dyes or allow the uses of silicone adhesives with sterile product to prevent or preclude biofilm from forming on wounds.

There is thus a need for new methods of making dressings and other medical devices with absorbed or impregnated therapeutic agents, more specifically antimicrobial positive and negative dyes, where the medical devices' performance is not impaired by an EO sterilization step. The above noted teachings do not aid in the resolution of a number of practical difficulties that are resolved by the present invention.

SUMMARY OF THE INVENTION

The present invention describes a sterilized compression bandage for treating wounds comprised of an elongated polymer foam layer preferably about 3 mm in thickness and ranging from 1.5 to about 5 mm in thickness which is placed over the skin and wound. The foam layer contains a plurality of antimicrobial dyes with at least one dye being gram positive and at least one other dye which is gram negative and a biofilm reduction agent. An elongated elastic compression wrap is secured to the elongated polymer foam layer by adhesive to hold the composite compression bandage in place against the wound.

It is an object of the invention to make sterilized compression bandages with one or more foam layers, each of which can be infused with antimicrobial gram positive and gram negative dyes and other useful agents.

It is another object of the invention to design a kit containing a two layer compression bandage with woven compression material constituting one layer and a dyed polyurethane foam infused with gram positive and gram negative dye to form an antimicrobial comfort layer mounted to the compression material layer. The kit also contains an elastic sleeve which is mounted over the wrapped compression bandage.

It is still another object of the invention to design a sterile kit containing a two layer compression bandage with woven compression material constituting one layer and a dyed polyurethane foam infused with gram positive and gram negative dye and an enzyme biofilm inhibitor, the combination forming an antimicrobial layer which contacts the skin of the patient mounted to the compression material layer.

It is yet another object of the invention to provide an effective wound dressing comprising antimicrobial polymer for the treatment of wrapped wounds that is capable of adsorbing moisture and exudate for optimal wound healing.

BRIEF DESCRIPTION OF THE DRAWINGS

The present invention will be described with reference to the appended Figures, in which.

These and other objects, advantages, and novel features of the present invention will become apparent when considered with the teachings contained in the detailed disclosure along with the accompanying drawings.

DESCRIPTION OF THE INVENTION

Use of the singular herein includes the plural and vice versa unless expressly stated to be otherwise, or obvious from the context that such is not intended. That is, "a" and "the" refer to one or more of whatever the word modifies. For example, "a device" includes one device, two devices, etc. Likewise, "a polymer" may refer to one, two or more polymers, and "the polymer" may mean one polymer or a plurality of polymers. By the same token, words such as, without limitation, "devices "and "polymers" would refer to one device or polymer as well as to a plurality of devices or polymers unless, again, it is expressly stated or obvious from the context that such is not intended.

In the same manner, any ranges presented are inclusive of the end-points. For example, "a temperature between 10° C. and 30° C." or "a temperature from 10° C. to 30° C." includes 10° C. and 30° C., as well as any temperature in between.

Also, words of approximation when used herein such as, without limitation, "about" "substantially," "essentially" and "approximately" mean that the word or phrase modified by the term need not be exactly that which is written but may vary from that written description to some extent. The extent to which the description may vary will depend on how great a change can be instituted and have one of ordinary skill in the art recognize the modified version as still having the properties, characteristics and capabilities of the modified word or phrase. In general, but with the preceding discussion in mind, a numerical value herein that is modified by a word of approximation may vary from the stated value by .+−0.15%, unless expressly stated otherwise.

The aspects of the present invention are described in the following paragraphs along with their preferred embodiments. In the below text the term "wound" is to be understood in its broadest sense, i.e. as any exterior part of a human or animal body that may be in need of treatment, particularly antibacterial treatment. Examples of wounds in the present context include but are not limited to: Any laceration to the skin, such as a wound, a chronic wound, a burn wound, a cut, wounds associated with dermatological conditions, grafts, pressure wounds, traumatic wounds, underlying infections with fistulation from bone, joint or soft tissue. The present invention uses polymeric foam or sponges treated with antimicrobial material which is placed over the wound.

There is currently a need for effective medical products that include active substances which inhibit the growth of and/or kill bacteria, fungi, virus in particular there is a need for wound care products that inhibit the growth of and/or reduce biofilm forming bacteria more efficiently.

Wound Dressing Materials

Figure 1:
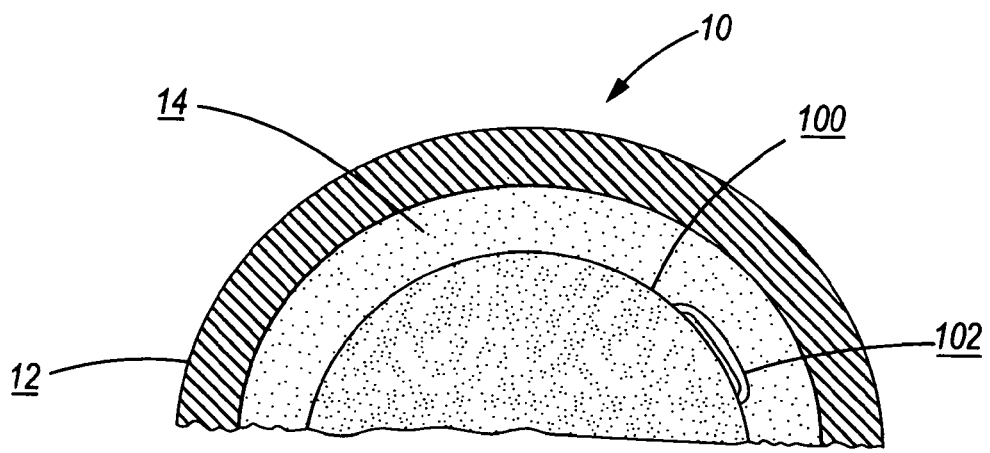
FIG. 1 is an enlarged partial cross section of the two layer compression wrap.
Figure 2:
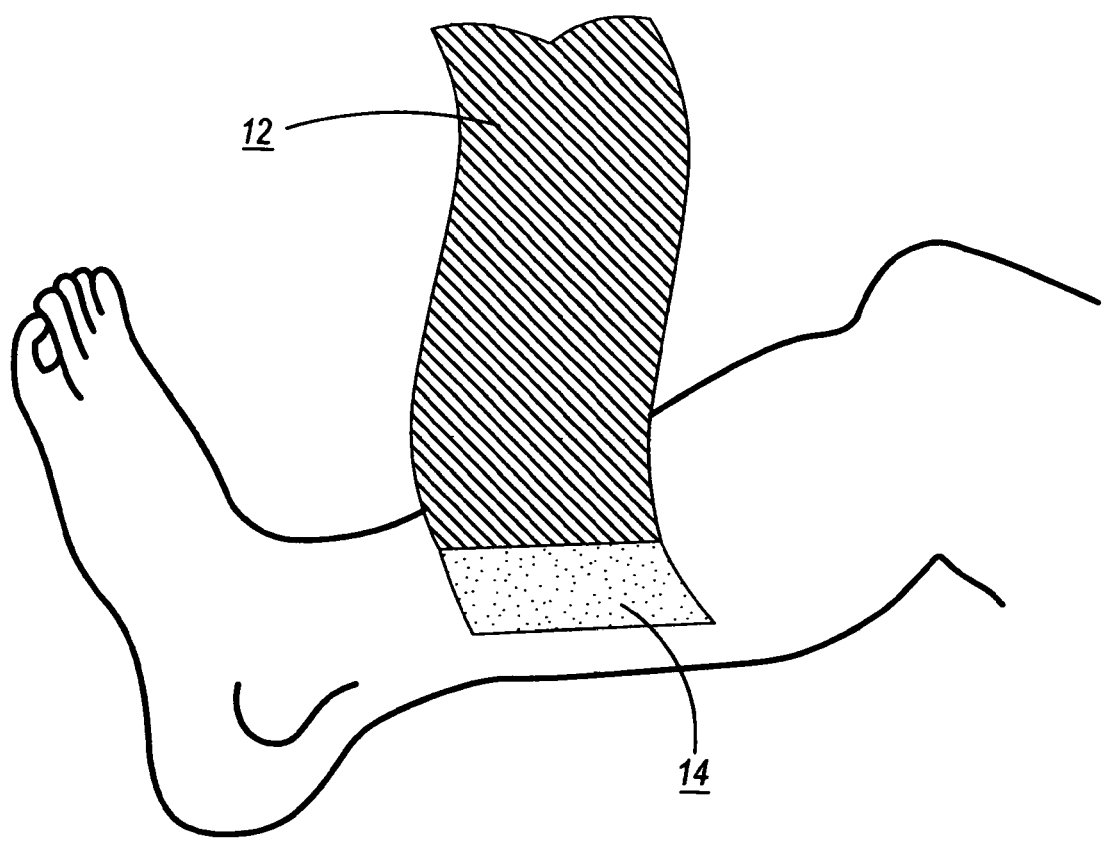
FIG. 2 is a perspective view of the invention showing a smaller foam section which contacts the skin of the user mounted to the compression layer of the compression bandage.
Figure 3:
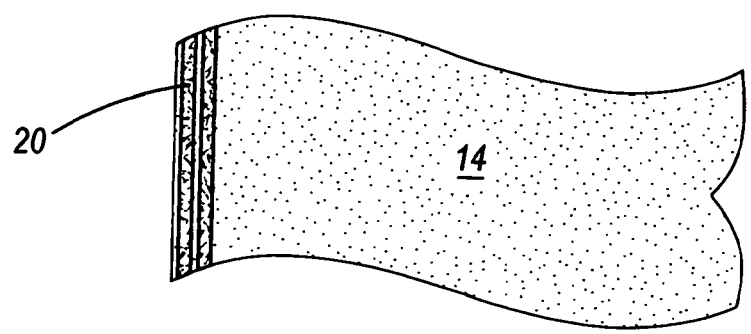
FIG. 3 is a partial bottom plan view of the foam comfort layer using strips of silicone adhesive at the end of the foam layer allowing the foam layer to be secured to the skin.
Figure 4:
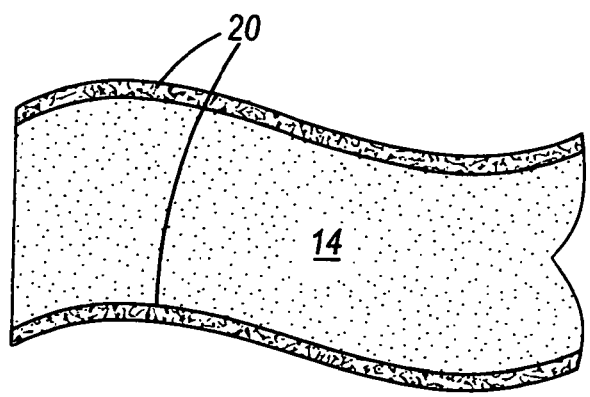
FIG. 4 is a partial bottom plan view of another embodiment of the foam comfort layer using strips of silicone adhesive along the sides of the foam layer allowing the foam layer to be secured to the skin.
Figure 5:
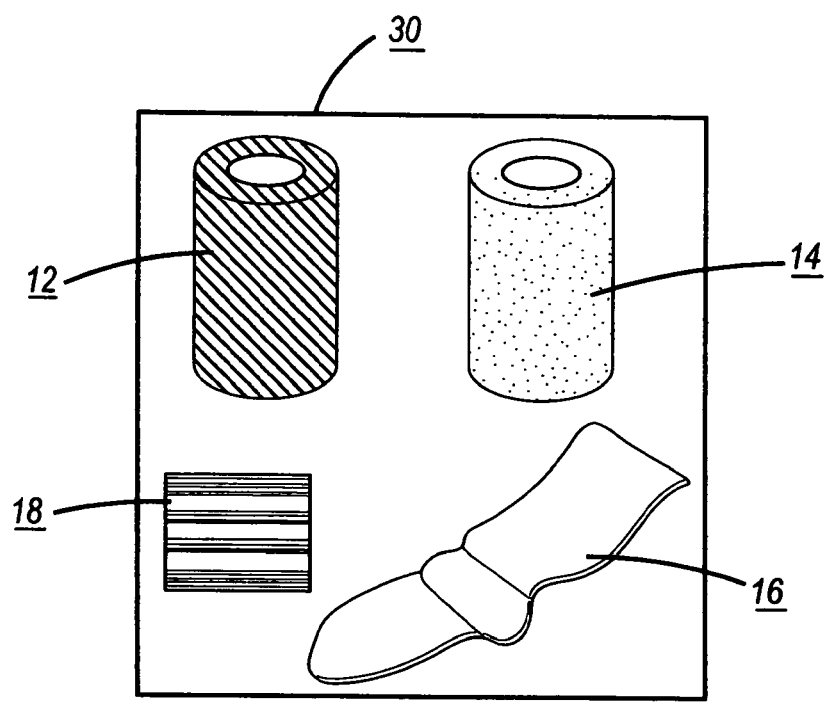
FIG. 5 is a kit shown schematically including both layers of the compression bandage separated from each other as separate rolls, a fastener and elastic sleeve.

The present invention is shown in FIGS. 1-4 and a kit 30 containing same is shown in FIG. 5. The antimicrobial compression device 10 can have a plurality layers; a compression layer 12 and an antimicrobial absorbent foam comfort layer 14 which can be combined in a number of ways that have a therapeutic value. The antimicrobial comfort layer 14 is the contact layer with the skin 100 or wound 102 and provides a non-abrasive comfort layer for the wound surface. The base dressing material of the comfort layer 14 can be made from a number of polymers or fibers known in the art. In a preferred embodiment the base dressing is a polyurethane foam.

The wound comfort layer 14 may be a foam or sponge material and is preferably polymeric in composition where the polymer can be a synthetic substance, a natural substance or combinations thereof. In one example the synthetic polymer can be polyvinyl formal, polyvinyl acetal, polyurethane, polyester or a mixture of polymers. It should be noted that the term layer is either referred to as a foam or sponge and these terms can be interchanged with the same meaning. The natural polymer material can be either animal or plant derived, for example, collagen, or chitosan. The preferred sponge material is polyurethane. The sponge material may also be polyvinyl formal or polyvinyl acetal.

The polyurethane foam or sponge has a morphology characterized by an average pore throat diameter of 0.5-800 pm, a fluid retention of 5.5-25.0 mL fluids/g porous material, a density of 0.05-0.15 g polymer/cm$^3$ porous material, (with a preferred density of about 0.09 to about 0.11 g polymer/cm$^3$) and a total porosity of 60-99.5%. The cell structure is characterized as open/interconnected with through pores that can be evaluated by techniques such as capillary flow, porosity and liquid extrusion porosimetry.

The antimicrobial foam comfort layer 14 when used in a compression wrap 10 as shown in FIGS. 1-4. and can be of any length, width and thickness. The foam layer 14 length can range from about 2 feet to about 15 feet long, more preferably 3-9 feet long and most preferably 4 feet long. The foam layer width may be about 1.5 inches to about 8 inches wide and more preferably 2, 4, or 6 inches wide. The foam layer width ranges in thickness from about 0.5 to about 10 mm, more preferably about 2-6 mm thick and most preferably 3-5 mm thick. A third layer formed by a stocking or sleeve 16 may comprise woven or non-woven material and is used to hold the compression wrap in place. Sleeve size can be of any range needed to fit a patient and may further have a lubricious coating to aid in putting it on or taking it off of a patient or user.

The comfort foam layer 14 is comprised of a foam dressing material with gram positive and gram negative dyes attached to the foam material as noted below.

The dyes used in the foam layer or additionally in the stretch fabric are clinically safe and have antimicrobial properties. The term "antimicrobial" is defined as having the ability to destroy or inhibit the growth of microorganisms, and comprises one or more of the following: antibacterial, antifungal, antiprotozoal, and antiviral.

Dyes can include, for example, triaryl or diarylmethanes, methylene blue, toluidine blue, methylene violet, azure A, azure B, azure C, brilliant cresol blue, thionin, methylene green, bromcresol green, gentian violet, acridine orange, brilliant green, acridine yellow, quinacrine, trypan blue, trypan red and mixtures of these dyes. In a preferred embodiment, the dyes are methylene blue and gentian violet. The above dye listing contains gram positive and gram negative dyes. Dyes of both gram types are utilized to combat a large family of bacteria and other microorganisms having gram positive and gram negative characteristics.

In the preferred embodiment the comfort layer is a 3 mm thick polyurethane foam, dyed with methylene blue and gentian violet. The foam is cut to a four inch width and a four foot dimension and rolled. In addition to its antimicrobial properties, the foam layer 14 should provide padding, skin protection, and the ability to distribute pressure evenly.

The compression layer 12 applies a therapeutically beneficial level of pressure in the working or resting state to the area of treatment; ankle, calf, leg, etc. The compression layer 12 is preferably a layer placed on or wrapped over the antimicrobial comfort layer 14 and can be a compression bandage or a compression wrap. It is recognized that more than one compression layer may be used to achieve a therapeutically effective dosage of pressure (mm Hg), when the patient's ankle-brachial index (ABI) is greater or equal to 0.5 and 30-40 mm Hg when the patient's ABI is greater or equal to 0.8. These materials differ when the compression material is a short stretch or long stretch bandage or wrap.

Fixation Element

One fixation element for securing the two layers 12 and 14 together or the bottom foam layer 14 to the skin 100 are adhesive silicone strips 20 or a permeable adhesive. The strips 20 can be placed perpendicular to the axis of the layer as shown in FIG. 3 or placed parallel to the axis of the layer as shown in FIG. 4. When the layers 12 and 14 are attached to each other, VELCRO and metal toothed clamping clips (not shown) can be used.

Biofilm Reduction Agents

Biofilm reduction agents are clinically safe and help remove biofilm by breaking up the film structure. Such agents are incorporated onto the sponge layer 14.

As an example, enzymes are used to target and break down the extracellular polymer substances of the biofilm and include amylase enzymes (e.g. amyloglucosidase, bacterial amylo novo), protease enzymes (e.g. savinase and everlase) fibrinolytic agents (e.g. plasmin, streptokinase, and nattokinase, and TrypLE), deoxyribonuclease I, glycoside hydrolase dispersin B, and cellulose.

Cheleating Agents and Surfactants

Also chelating agents are used in the sponge body to sequester the metals that crosslink polysaccharides in the biofilm including ethylenediaminetetraacetic acid (EDTA), citrates, phosphonates and phosphoric acids.

Surfactants are added to the sponge layer 14 and are used to solubilize the biofilm macromolecules, including ionic and nonionic surfactants. Ionic surfactants may be negatively charged, positively charged, or zwitterionic, and include alkyl sulfates (e.g. sodium dodecyl sulfate), alkyl carboxylates, (e.g. sodium stearate), tertiary or quaternary alkyl ammoniums (e.g. cetrimonium bromide, cetrimonium chloride, cetrimonium stearate), 3-[(3-cholamidopropyl)dimethylammonio]-1-propanesulfonate (CHAPS). Non-ionic surfactants may include polyethylene glycol, polyethylene oxide, Triton, Tergitol, Pluronics, IGEPELS, Tweens, fatty acid esters.

Example 1

PU foam, PVA and PVAf foam were dyed with methylene blue (MB) and crystal violet (CV) or gentian violet, washed with water and dried. The dyed foam or sponge layers 14 were then processed through gamma irradiation and/or sterilization EO steps to obtain test units.

Gamma Irradiation 25-36 kilogray (kGy) dose achieved by controlled exposure to Cobalt 60.

EO Terminal Sterilization

Pre-Conditioning: N/A

Cycle Temperature: 108+ or −5° F.

Cycle Humidity: approximately 30% RH

Sterilant (EO) Concentration: approximately 600 mg/L

Data shows surprising results with an increase in antibacterial dye effectiveness for both the PVA and PU foam or sponges which is normally reduced during the sterilization step and allows the use of silicone adhesive on the sponges treated with EO sterilization.

Antibacterial Compression Kit

The antimicrobial comfort layer 14 is rolled and packaged in a sterile barrier pouch and sterilized with 25-40 kGy gamma irradiation. The sterile packaged antimicrobial comfort layer 14 is placed into a kit box 30 along with a 4 inch times 5.1 yard rolled short stretch elastic bandage 12 (CO-FLEX®), a fixation member 18 for fastening the foam layer 14 and elastic layer 12, together and an elastic stocking or sleeve 16 (covering element), The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What is claimed is:

1. A bandage for treating wounds comprising a polymer containing an antimicrobial agent, wherein said polymer comprises polyvinyl acetal, polyurethane, or a mixture of said polymers, wherein said antimicrobial agent comprises an antimicrobial dye comprising a gram positive dye and a gram negative dye, wherein said polymer is gamma irradiated, wherein said polymer is treated with EO sterilization, and wherein said gamma irradiation increases antimicrobial agent effectiveness of said polymer treated with EO sterilization.

2. The bandage of claim 1 wherein said polymer is gamma irradiated prior to said polymer being treated with EO sterilization.

3. The bandage of claim 1 wherein said antimicrobial agent is taken from a group of dye consisting of triaryl or diarylmethanes, methylene blue, toluidine blue, methylene violet, azure A, azure B, azure C, brilliant cresol blue, thionin, methylene green, bromcresol green, gentian violet, acridine orange, brilliant green, acridine yellow, quinacrine, trypan blue, trypan red and mixtures of these dyes.

4. The bandage of claim 1 wherein said polymer is a polyurethane.

5. The bandage of claim 1 wherein said polymer comprises polyvinyl acetal.

6. The bandage of claim 1 wherein said gram positive dye and said gram negative dye are methylene blue and gentian violet.

7. The bandage of claim 1 wherein said polymer comprises a foam.

8. The bandage of claim 7 wherein said foam comprises polyurethane.

9. The bandage of claim 8 wherein said polymer is gamma irradiated prior to said polymer being treated with EO sterilization.

10. The bandage of claim 7 wherein said foam has a morphology characterized by an average pore throat diameter of 0.5-800 μm, a fluid retention of 5.5-25.0 mL fluids/g porous material, and a density of 0.05-0.15 g polymer/cm$^3$ porous material.

11. The bandage of claim 10 wherein said foam is interconnected by pores suitable to provide capillary flow and has a density ranging from about 0.09 to about 0.11 g polymer/cm$^3$ porous material.

12. The bandage of claim 7 further comprising a silicone adhesive.

13. The bandage of claim 12 where said silicone adhesive is in the form of a plurality of adhesive strips secured to said foam.

* * * * *